(12) United States Patent
Hayes et al.

(10) Patent No.: US 6,367,340 B1
(45) Date of Patent: Apr. 9, 2002

(54) TRANSFER MECHANISM FOR ENVIRONMENTAL TESTING APPARATUS

(75) Inventors: Robert K. Hayes, Fruitport; Clinton A. Peterson, Holland, both of MI (US)

(73) Assignee: Venturedyne, Ltd., Milwaukee, WI (US)

( * ) Notice: Subject to any disclaimer, the term of this patent is extended or adjusted under 35 U.S.C. 154(b) by 0 days.

(21) Appl. No.: 09/518,715

(22) Filed: Mar. 3, 2000

(51) Int. Cl.$^7$ .............................................. G01N 17/00
(52) U.S. Cl. ...................................... 73/865.6; 374/57
(58) Field of Search ........................... 73/865.6; 374/45, 374/57

(56) References Cited

U.S. PATENT DOCUMENTS

| | | | | |
|---|---|---|---|---|
| 4,282,181 A | * | 8/1981 | Pierce | 73/865.6 X |
| 4,519,718 A | * | 5/1985 | Staffin et al. | 374/45 |
| 5,167,451 A | * | 12/1992 | Müller et al. | 374/45 |
| 5,191,282 A | * | 3/1993 | Liken et al. | 324/760 X |
| 5,269,370 A | * | 12/1993 | Christian et al. | 374/57 X |
| 5,646,813 A | * | 7/1997 | Jon et al. | 73/865.6 X |
| 5,752,771 A | * | 5/1998 | Ping et al. | 374/57 |
| 6,101,083 A | * | 8/2000 | Artz et al. | 73/865.6 X |

FOREIGN PATENT DOCUMENTS

| | | | | |
|---|---|---|---|---|
| JP | 57-151842 | * | 9/1982 | 73/865.6 |
| JP | 60-263836 | * | 12/1985 | 374/57 |
| JP | 3-120441 | * | 5/1991 | 374/57 |
| JP | 3-158740 | * | 7/1991 | 374/57 |
| JP | 4-43940 | * | 2/1992 | 374/57 |
| SU | 834951 | * | 5/1981 | 73/865.6 |
| SU | 1578596 | * | 7/1990 | 73/865.6 |

OTHER PUBLICATIONS

Derwent Abstract of SU 1251043 A2 Inventor Rumshevich Thermochamber e.g. for Electronics Components Testing—Uses Movable Platform Mounted in Test Volume and Used for Mounting Tested Items, Aug. 1986.*

TDB–ACC–No.: NN 86 123182 Baskets for Environmental Module Testing: IBM Technical Disclosure Bulletin, vol. 29, No. 7, p. 3182, Dec. 1986.*

* cited by examiner

*Primary Examiner*—Thomas P. Noland
(74) *Attorney, Agent, or Firm*—Jansson, Shupe & Munger, Ltd.

(57) ABSTRACT

An apparatus for conducting environmental tests on a device and which incorporates an improved transfer mechanism is provided. The apparatus includes a cabinet defining first and second chambers therein. An insulation wall extends between the testing chambers and has an opening therein so as to allow passage between the first and second testing chambers. The transfer mechanism includes a frame structure positioned within the cabinet for supporting a basket which carries the device to be tested. The basket is slidable along the supports of the frame structure for carrying the device between the first and second testing chambers.

20 Claims, 5 Drawing Sheets

TRANSFER MECHANISM FOR
ENVIRONMENTAL TESTING APPARATUS

FIELD OF THE INVENTION

This invention relates generally to environmentally controlled testing equipment, and in particular, to an environmental test apparatus having first and second environmentally controlled testing chambers and which incorporates a transfer mechanism for transferring products to be tested between the testing chambers.

BACKGROUND AND SUMMARY OF THE PRESENT INVENTION

Many types of devices or products undergo testing to improve the quality and reliability of the devices. Typically, these types of devices undergo a series of environmental tests under various combinations of temperature, humidity, and other climatic conditions to insure product reliability and performance in extreme environmental conditions. Further, many of these devices are tested to insure that the devices are not adversely effected when operated in a common environment with a plurality of other such devices.

In order to test their devices, manufacturers often utilize an environmental test apparatus which is capable of producing rapid and extreme changes in temperature, humidity and other climatic conditions. A prominent designer and manufacturer of such environmental test apparatus is Thermotron Industries, Inc. of Holland, Mich.

Often times, these types of tests are conducted with a single testing chamber. The climatic conditions within the testing chamber are controlled by heating, humidity and air conditioning units which generate the rapid changes in climatic conditions within such testing chamber. Alternatively, first and second testing chambers may be provided. The environments within the testing chambers are independently controlled by separate heating, humidity and air conditioning units. A basket carries the devices to be tested between the testing chambers. An insulation space is provided between the testing chambers in order to limit the transfer of heat therebetween.

Heretofore, the basket would be mounted within a basket frame. The basket is centrally located within the frame so as to provide air gaps on opposite sides of the basket of lengths generally equal to the thickness of the insulation space provided between the testing chambers. The air gaps are necessary to act as an insulation space between the basket located in one of the testing chambers and the other testing chamber. As such, the height of the product carrying cavity in the prior art basket is equal to the height of the basket frame minus twice the thickness of the insulation space provided between the testing chambers. The limitations on the size of the product carrying cavity in the basket reduces the volume available in the basket to hold product during testing. Consequently, by limiting the volume available for product, the number of products which may be tested at a single time with environmental test apparatus is correspondingly limited. Alternatively, if greater volume within the basket is not necessary, the size of the environmental test apparatus must still accommodate the basket and the air gaps.

Therefore, it is a primary object and feature of the present invention to provide a transfer mechanism for an environmental test apparatus which incorporates a basket of a greater volume than prior baskets.

It is a still further object and feature of the present invention to provide a transfer mechanism for an environmental test apparatus having first and second environmentally controlled testing chambers which environmentally isolates one of the testing chambers from the other.

It is a still further object and feature of the present invention to provide a transfer mechanism for an environmental test apparatus which is simple to operate and inexpensive to manufacture.

In accordance with the present invention, an apparatus is provided for conducting an environmental test on a device. The apparatus includes a cabinet defining first and second testing chambers therein. An isolation wall extends between the testing chamber and has an opening therein so as to allow passage between the first and second testing chambers. A sealing structure is positioned within the cabinet and includes first and second sealing members interconnected by a support element. The sealing structure is movable between a first position wherein the first sealing member engages the first side of the insulation wall and overlaps the opening therein and a second position wherein the second sealing member engages the second side of the insulation wall and overlaps the opening therein. A basket is provided for carrying the device to be tested. The basket is movable along the support element of the sealing structure between a first position adjacent the first sealing member and a second position adjacent the second sealing member. An actuator extends through one of the sealing members and is interconnected to the basket. The actuator controls movement of the basket between the first and second positions. A control structure may be operatively connected to the cabinet for independently controlling environmental conditions within the testing chamber.

First sealing member includes a generally flat plate having a seal affixed thereto. The seal of the first sealing member engages the first side of the insulation wall with the sealing structure in the first position. The second sealing member includes a generally flat plate having a seal affixed thereto. The seal of the second sealing member engages the second side of the insulation wall with the sealing structure in the second position.

The support element of the sealing structure includes a shaft extending between the first and second sealing members. The basket includes a guide therethrough. The shaft of the support structure extends through the guide in order to guide the basket between the first and second positions.

In accordance with the still further aspect of the present invention, an apparatus is provided for conducting environmental tests on a device. The apparatus includes a cabinet defining first and second testing chambers therein. An insulation wall is disposed within the cabinet between the testing chambers. The insulation wall includes first and second spaced panels interconnected by a third panel of predetermined length. The third panel is perpendicular to the first and second panels so as to define an opening in the insulation wall which allows passage between the first and second testing chambers. A frame structure is positioned within the cabinet and includes first and second sealing panels interconnected by at least one support of predetermined length. The frame structure is movable between a first position wherein the first sealing panel engages the first panel of the insulation wall and overlaps the opening therein and a second position wherein the second sealing panel engages the second panel of the insulation wall and overlaps the opening therein. A basket is supported by the frame structure. The basket carries the device to be tested and has a length, height and depth. The height of the basket is generally equal to the difference between the length of the at least one support of the frame structure and the length of the third panel of the insulation wall.

The basket is slidable along the at least one support of the frame structure between the first position adjacent the first sealing panel and a second position adjacent the second sealing panel. The basket may include a guide tube having a passageway therethrough. The shaft of the support structure extends through the passageway and the guide tube so as to guide the basket between the first and the second positions. An actuator extends through one of the sealing members and is interconnected to the basket. The actuator controls movement of the basket between first and second positions.

The first sealing panel of the frame structure includes the seal affixed thereto. The seal of the first sealing panel engages the first panel of the insulation wall with the frame structure in the first position. The second sealing panel of the frame structure also includes a seal affixed thereto. The seal of the second sealing panel engaging the second panel of the insulation wall with the frame structure in the second position.

In accordance with a still further aspect of the present invention, an improvement in an environmental testing apparatus is provided. The environmental testing apparatus has first and second testing chambers and an insulation wall disposed therebetween. The insulation wall has an opening therein so as to allow passage between the first and second testing chambers. The improvement comprises a frame structure positioned within the cabinet. The frame structure includes first and second sealing panels interconnected by at least one support. A basket carries the device to be tested within the environmental testing apparatus. The basket is slidable along the at least one support of the frame structure between a first position adjacent the first sealing panel and a second position adjacent the second sealing panel.

It is contemplated that the frame structure be movable between a first position wherein the first sealing panel engages a first side of the insulation wall and overlaps an opening therein, and a second position in the second sealing panel engages the second side of the insulation wall and overlaps the opening therein. The first sealing panel includes a seal affixed thereto. The seal of the first sealing panel engages the first side of the insulation wall with the frame structure in the first position. The second sealing panel also includes a seal affixed thereto. The seal of the second sealing panel engaging the second side of the insulation wall with the frame structure in the second position.

The basket includes a guide therethrough. The support of the frame structure extends through the guide and guides the basket between the first and second positions. An actuator extends through one of the sealing panels and is interconnected to the basket. The actuator controls movement of the basket between the first and second positions.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
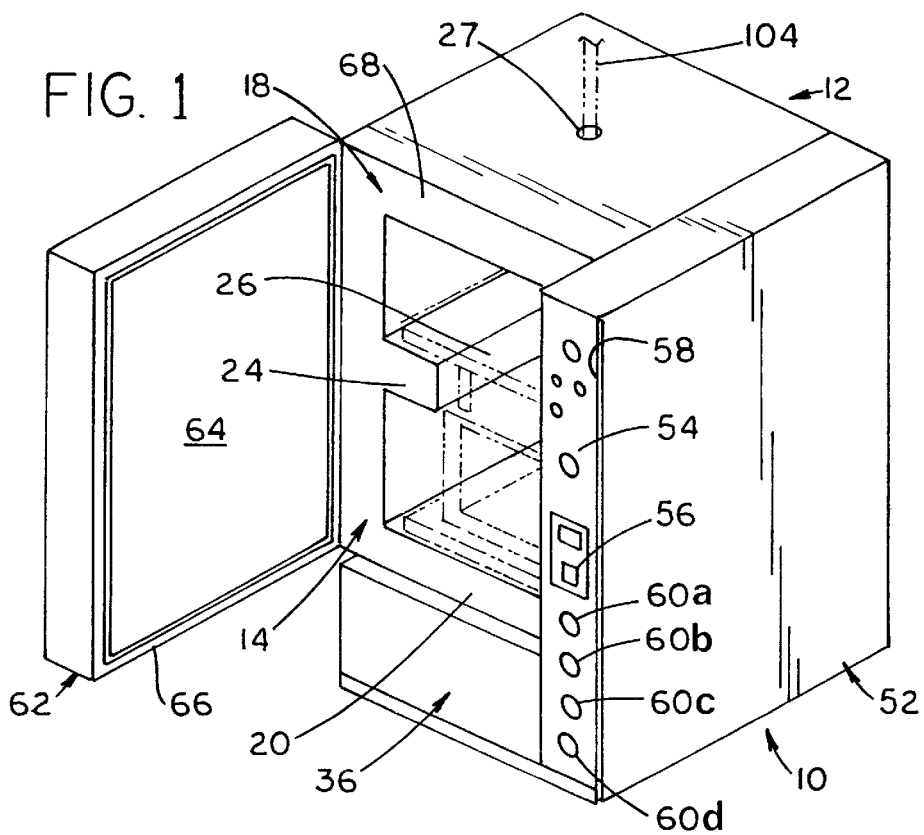
FIG. 1 is an isometric view of an environmental test apparatus for receiving a transfer mechanism in accordance with the present invention.
Figure 2:
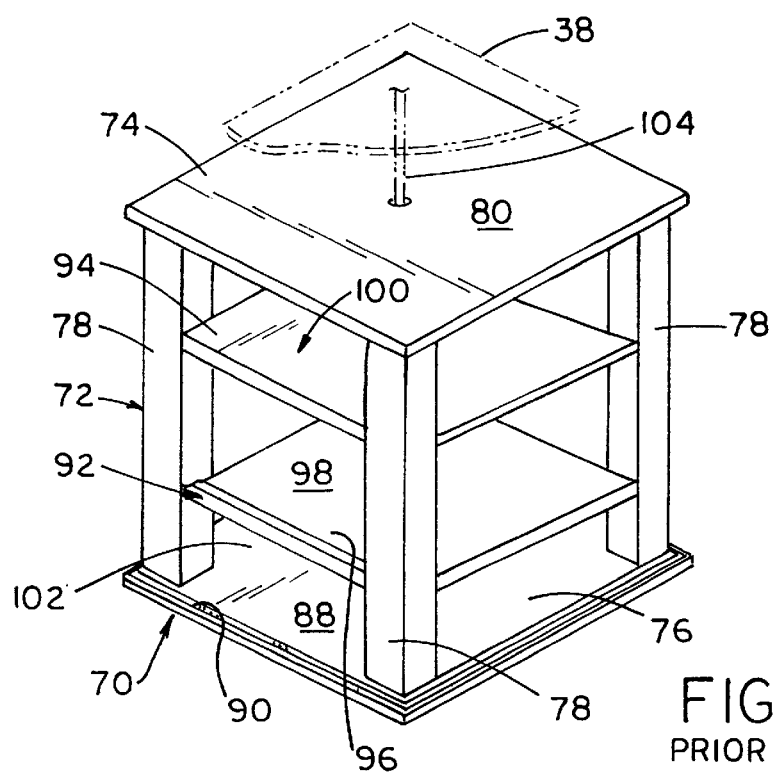
FIG. 2 is an isometric view of a prior art transfer mechanism.

Referring to FIG. 1, an environmental test apparatus is generally designated by the reference numeral 10. Environmental test apparatus 10 includes a body portion 12 defined by sidewalls 14 and 16, FIGS. 3–5 and 7–9, upper and lower walls 18 and 20, respectively, and rear wall (not shown). A generally horizontal insulation wall 24 is disposed between and upper and lower walls 18 and 20, respectively, and between sidewalls 14 and 16. Insulation wall 24 includes an opening 26 therein for reasons hereinafter described.

As best seen in FIGS. 3–5 and 7–9, sidewall 14 is defined by an inner panel 28 and an outer panel 30 having insulation disposed therebetween. Similarly, sidewall 16 is defined by an inner panel 29 and an outer panel 31 having insulation disposed therebetween.

Lower wall 20 of body portion 12 in environmental test apparatus 10 is defined by an inner panel 32 and an outer panel 34 having insulation disposed therebetween. It is contemplated to position outer panel 34 of lower wall 20 on a supporting base 36, FIG. 1, so as to support body portion 12 of environmental test apparatus 10 above a supporting surface, such as a floor of a laboratory or the like.

As is conventional, rear wall (not shown) in environmental test apparatus 10 is defined by an inner panel and an outer panel having insulation disposed therebetween. Body portion 12 further includes upper wall 18 projecting forwardly from rear wall. Upper wall 18 is defined by an inner panel 38 and an outer panel 40 having insulation disposed therebetween. One or more access ports 27 may extend through upper wall 18 in order to allow an actuator, as hereinafter described, to pass therethrough and/or to allow an operator to insert wiring, cabling or the like into environmental test apparatus 10.

Insulation wall 24 includes an upper panel 42 and a lower panel 44 having insulation disposed therebetween. A vertical wall 45 extends between upper panel 42 and lower panel 44 so as to define opening 26 in insulation wall 24. Upper panel 42 of insulation wall 24 and inner panel 38 of upper wall 18 define a first upper testing chamber 48 in environmental test apparatus 10. Lower panel 44 of insulation wall 24 and inner panel 32 of lower wall 20 define a second, lower testing chamber 50 within environmental test apparatus 10. As is conventional, the height $H_1$ of upper testing chamber 48 is generally equally to the height $H_1$ of lower testing chamber 50.

Referring back to FIG. 1, a controller housing 52 is mounted to and abuts outer panel 31 of sidewall 16. Controller housing 52 houses the controller (not shown) for the environmental conditioning units such as heaters, air conditioning units, and the like stored in supporting base 36. As is conventional, the heaters and air conditioning units in supporting base 36 independently vary the environmental conditions within upper testing chamber 48 and lower testing chamber 50 in response to commands from the controller.

Controller housing 52 includes a forwardly directed face 54 having a plurality of user interface devices mounted thereto. By way of example, such user interface devices may include a keypad 56 and function switches, collectively designated by the reference numeral 58. Keypad 56 and function switches 58 are interconnected to the controller (not shown) in order to allow an operator to reset the climatic conditions within upper testing chamber 48 and lower testing chamber 50 within body portion 12 during testing. A plurality of analog gauges and/or dials 60a–60d are mounted to forwardly directed face 54 of controller housing 52. Dials 60a–60d may be interconnected to sensors (not shown) which measure pressures within the various climatic conditioning units in the body portion 12. It is contemplated to interconnect the controller, heaters, air conditioning units and other climatic conditioning units to a power source (not shown).

Environmental test apparatus 10 further includes a door 62 having an inner panel 64 and an outer panel having insulation disposed therebetween. Door 62 is pivotably mounted to outer panel 30 of sidewall 14 of body portion 12 by hinges so as to allow door 62 to pivot thereon between a closed position and an open position, FIG. 1. As is conventional, a conductive gasket 66 may be mounted to inner panel 64 of door 62 about the outer periphery thereof. With door 62 in a closed position, conductive gasket 66 abuts outwardly directed face plate 68 of body portion 12 so as to form a seal between door 62 and body portion 12 thereby isolating the environments within testing chambers 48 and 50 from the environment outside environmental test apparatus 10.

In order to transfer a product between upper testing chamber 48 and lower testing chamber 50, a transfer mechanism must be used. Referring to FIGS. 2–5, a prior art transfer mechanism is generally designated by the reference numeral 70. Prior art transfer mechanism 70 includes a frame structure 72 formed from generally rectangular upper and lower sealing panels 74 and 76, respectively. Upper and lower sealing panels 74 and 76, respectively, are generally parallel to each other and spaced from each other by a plurality of vertical supports 78. The length of supports 78 are generally equal to the height $H_1$ of one of the testing chambers 48 or 50 plus the height $HW_1$ of vertical wall 45 of insulation wall 24.

Upper sealing panel 74 of frame structure 72 includes an upper surface 80 and a lower surface 82. A seal 84 is mounted to lower surface 82 of upper sealing panel 74 radially outwardly of supports 78. Lower sealing panel 76 includes a lower surface 86 and an upper surface 88. A seal 90 is mounted to upper surface 88 of lower sealing panel 76 radially outwardly of supports 78.

A basket 92 is mounted within frame structure 72. Basket 92 includes an upper basket panel 94 and a lower basket panel 96 which defines a product receiving cavity 98 therebetween for receiving the products to be tested within environmental test apparatus 10. Basket 92 is centrally located between upper sealing panel 74 and lower sealing panel 76 of frame structure 72 such that an upper air gap 100 is provided between upper basket panel 94 and upper sealing panel 74 and a lower air gap 102 is provided between lower basket panel 96 and lower sealing panel 76. The widths of air gaps 100 and 102 are generally equal to the height $HW_1$ of vertical wall 45 of insulation wall 24.

Figure 3:
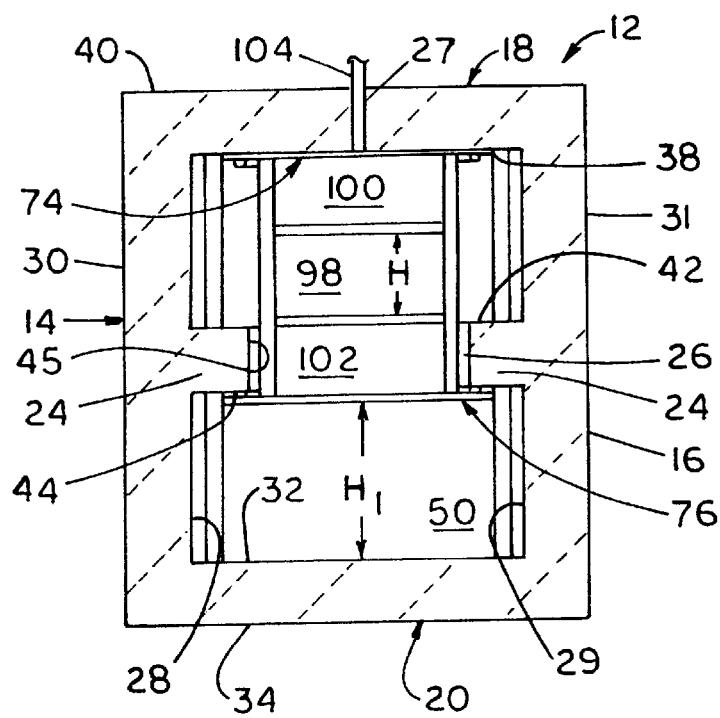
FIG. 3 is a front elevational view, partially in section, showing the prior art transfer mechanism of FIG. 2 in a raised position within an environmental test apparatus.

Referring to FIG. 3, in operation, transfer mechanism 70 is positioned within environmental test apparatus 10 such that upper sealing panel 74 is received within upper testing chamber 48 and lower seating panel 76 is received within lower testing chamber 50. Transfer mechanism 70 is movable between a first raised position, FIG. 3, wherein basket 92 is fully received within upper testing chamber 48 and a second, lowered position, FIG. 5, wherein basket 92 is fully received within lower testing chamber 50. An actuator 104 extends through access port 27 and is interconnected to upper sealing panel 74 to effectuate movement of transfer mechanism 70 between the raised position, FIG. 3, and the lowered position, FIG. 5. Actuator 104 may take the form of an air cylinder, a hydraulic cylinder, a linear screw actuator or other similar mechanism.

In the raised position, FIG. 3, lower sealing panel 76 overlaps opening 26 in insulation wall 24 such that seal 90 engages the lower panel 44 of insulation wall 24 so as to isolate the environment in upper testing chamber 48 from the environment in lower testing chamber 50. Air gap 102 provides an insulation space to further isolate the products within product receipt cavity 98 of basket 92 from the environment within lower testing chamber 50.

Figure 4:
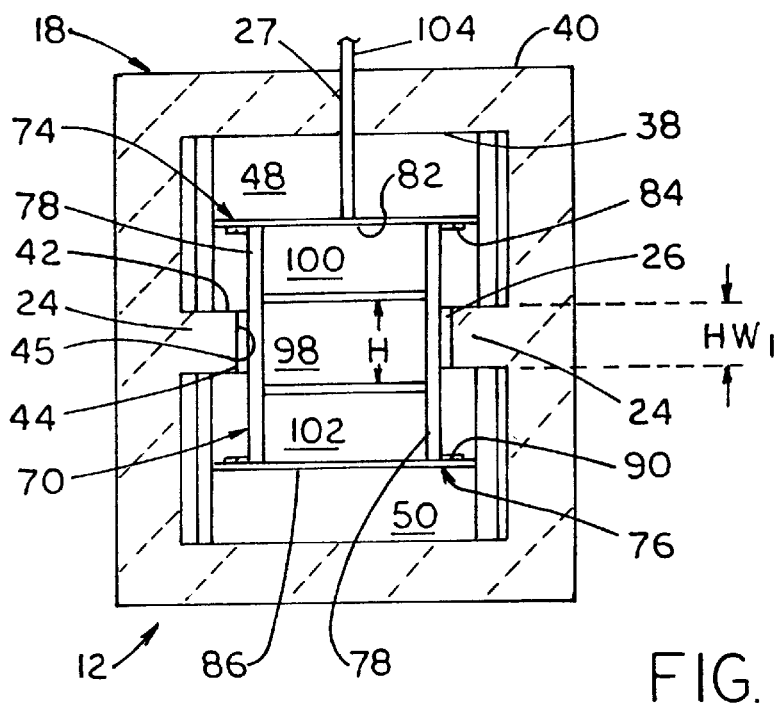
FIG. 4 is a front elevational view, partially in section, showing the prior art transfer mechanism of FIG. 2 in an intermediate position within an environmental test apparatus.
Figure 5:
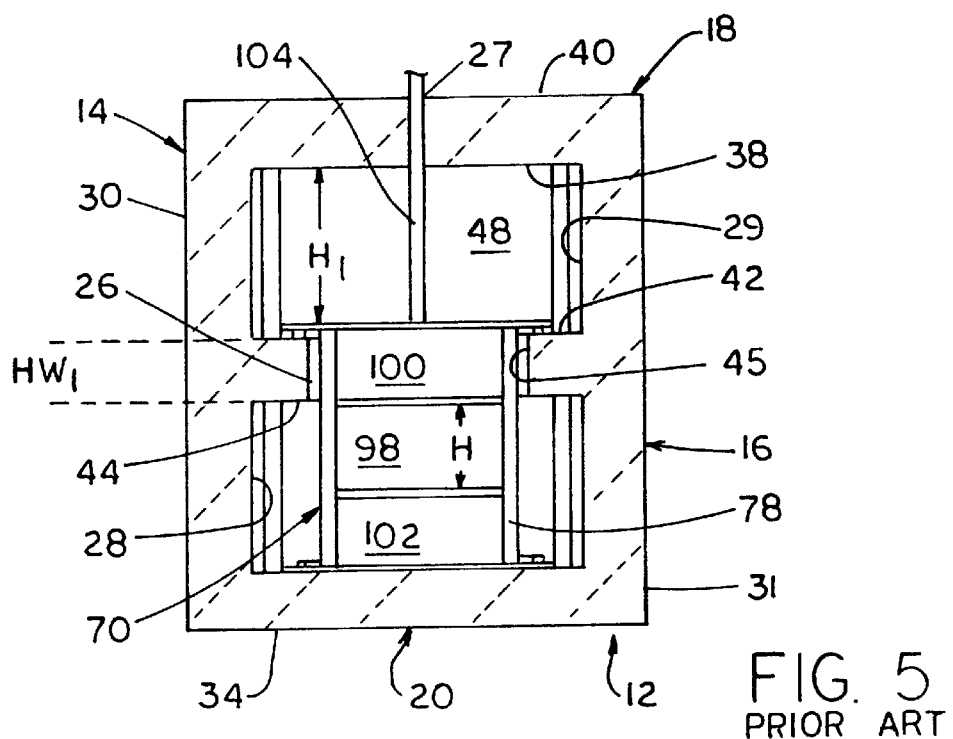
FIG. 5 is a front elevational view, partially in section, showing the prior art transfer mechanism in a lowered position within an environmental test apparatus.
Figure 6:
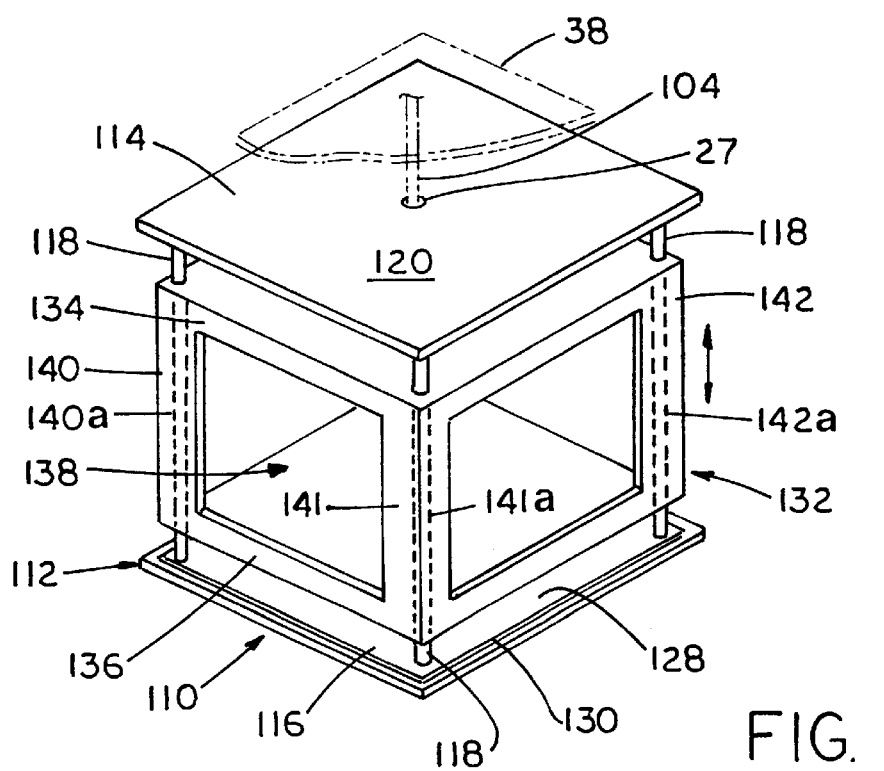
FIG. 6 is an isometric view of a transfer mechanism in accordance with the present invention.

As transfer mechanism 70 is lowered, FIG. 4, from the raised position, FIG. 3, to the lowered position, FIG. 5, seal 90 disengages from the lower panel 44 of insulation wall 24. In the lowered position, FIG. 5, upper sealing panel 74 overlaps opening 26 in insulation wall 24 such that seal 84 engages upper panel 42 of insulation wall 24 so as to isolate lower testing chamber 50 from the environment in upper testing chamber 48. Air gap 100 acts to further insulate the products to be tested within product receipt cavity 98 in basket 92 from the environment in upper testing chamber 48.

As described, in order to accommodate air gaps 100 and 102 in transfer mechanism 70, the height H of product receiving cavity 98 in basket 92 is limited to being no greater than the lengths of the supports 78 of frame structure 72 minus the widths of both air gaps 100 and 102. This, in turn, limits the number of products which may be inserted into product receipt cavity 98 and, hence, the number of products which may be tested at any one time.

In order to overcome the limitations on the height H of product receipt cavity 98 in prior art basket 92, a transfer mechanism 110 in accordance with the present invention is provided. As best seen in FIGS. 6–9, transfer mechanism 110 includes a frame structure 112 formed from generally rectangular upper and lower sealing panels 114 and 116, respectively. Upper and lower sealing panels 114 and 116, respectively, are generally parallel to each other and spaced from each other by a plurality of vertical supports 118. The length of supports 118 are generally equal to the height $H_1$ of one of the testing chambers 48 or 50 plus the height $HW_1$ of vertical wall 45 of insulation wall 24.

Upper sealing panel 114 of frame structure 112 includes an upper surface 120 and a lower surface 122. A seal 124 is mounted to lower surface 122 of upper sealing panel 114 radially outwardly of supports 118. Lower sealing panel 116 also includes a lower surface 126 and an upper surface 128. A seal 130 is mounted to upper surface 128 of lower sealing panel 116 radially outwardly of supports 118.

A basket 132 is slidably mounted within frame structure 112. Basket 132 is generally box-shaped and includes an upper basket panel 134 and a lower basket panel 136 which defines a product receiving cavity 138 therebetween for receiving the products to be tested within environmental test apparatus 10. Upper basket panel 134 and lower basket panel 136 are interconnected by guides 140, 141, and 142. Guides 140, 141, and 142 include corresponding passageways 140a, 141a, and 142a, respectively, therethrough. Supports 118 extend through corresponding passageways 140a, 141a, and 142a in guides 140, 141, and 142, respectively, such that basket 132 is allowed to slide along supports 118 between a first raised position, FIG. 7, and a second lowered position, FIG. 9.

Figure 7:
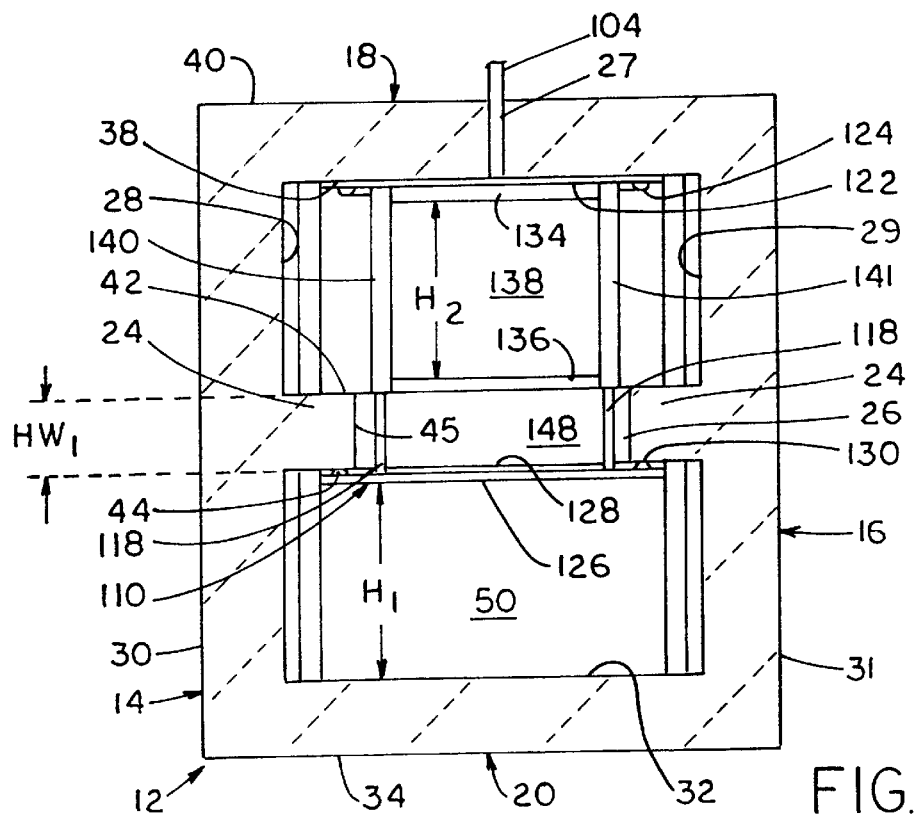
FIG. 7 is a front elevational view, partially in section, showing the transfer mechanism of the present invention in a raised position within the environmental test apparatus of FIG. 1.
Figure 8:
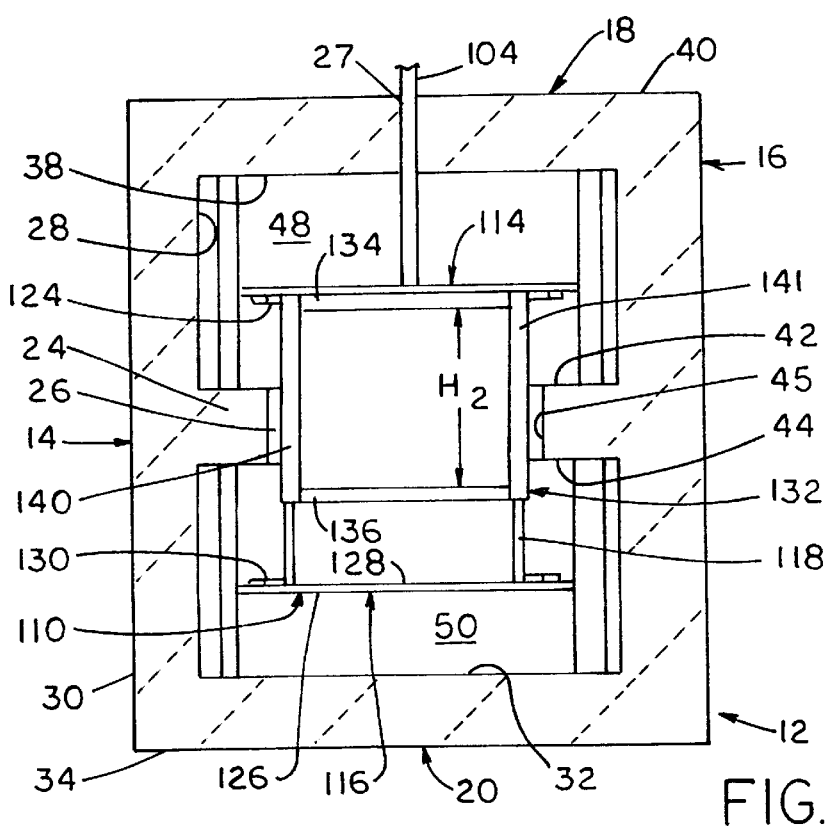
FIG. 8 is a front elevational view, partially in section showing the transfer mechanism of the present invention in an intermediate position within the environmental test apparatus of FIG. 1.
Figure 9:
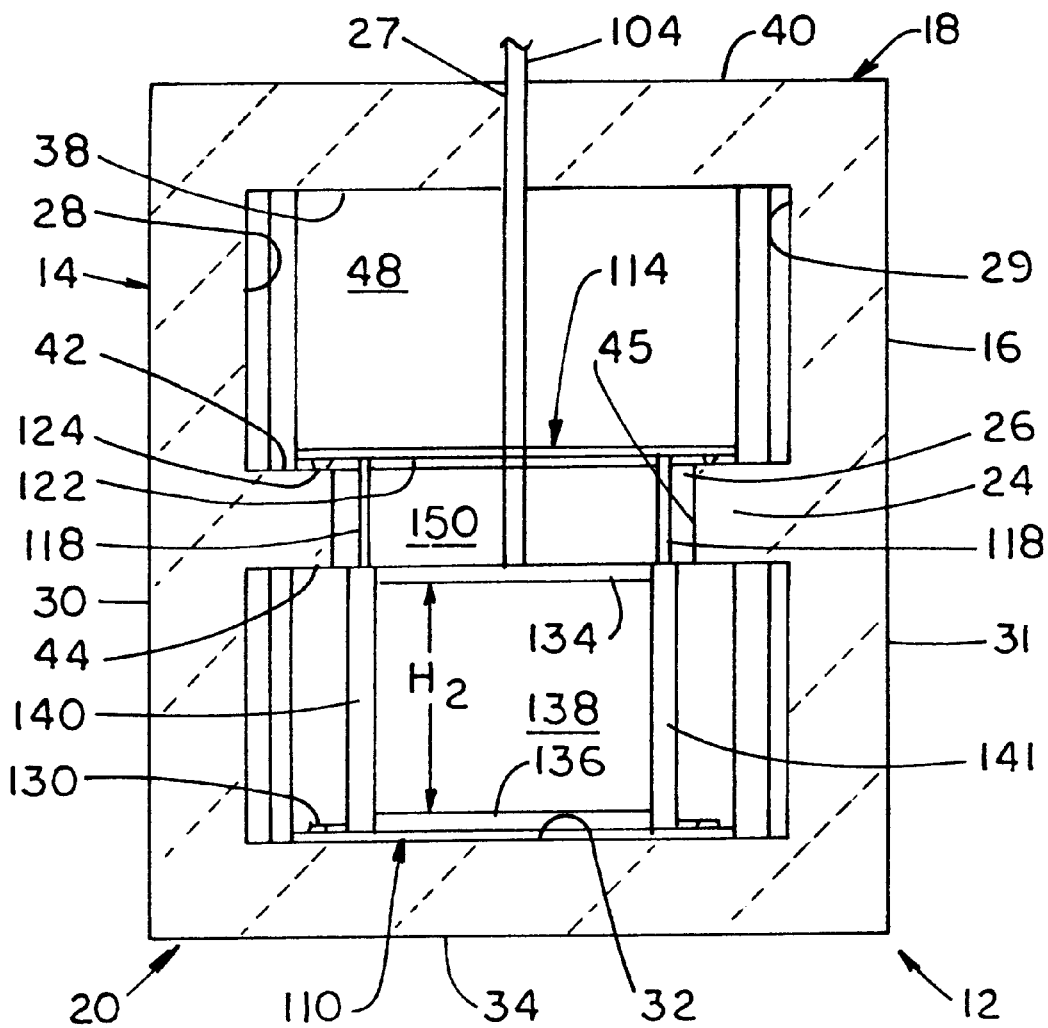
FIG. 9 is a front elevational view, partially in section, showing the transfer mechanism of the present invention in a lowered position within the environmental test apparatus of FIG. 1.

Referring to FIGS. 7–9, in operation, transfer mechanism 110 is positioned within environmental test apparatus 10 such that upper sealing panel 114 is received within upper testing chamber 48 and lower sealing panel 116 is received within lower testing chamber 50. Transfer mechanism 110 is movable between a first position of FIG. 7, wherein basket 132 is fully received within upper testing chamber 48 and a second, lowered position, FIG. 9, wherein basket 132 is fully received within lower testing chamber 50. Actuator 104 extends through access port 27 and through upper sealing panel 114, and is interconnected to upper basket panel 134 to effectuate movement of transfer mechanism 110 between the raised position, FIG. 7, and the lowered position, FIG. 9. As heretofore described, actuator 104 may take the form of an air cylinder, a hydraulic cylinder, a linear screw actuator or other similar mechanism. It is contemplated to bundle cable, wiring or the like with actuator 104 so as to electrically connect the product to be tested to various testing equipment and to allow such cabling, wiring or the like to travel with actuator 104.

In the raised position, FIG. 7, lower sealing panel 116 overlaps opening 26 in insulation wall 24 such that seal 130 engages the lower panel 44 of insulation wall 24 so as to isolate the environment in upper testing chamber 48 from the environment in lower testing chamber 50. In addition, upper basket panel 134 abuts lower surface 122 of upper sealing panel 114 and upper sealing panel 114 abuts inner panel 38 of upper wall 18 of body portion 12 of environmental test apparatus 10. An air gap 148 is defined between lower basket panel 136 and upper surface 128 of lower sealing panel 116 in order to provide the necessary insulation space to further isolate the product within product receipt cavity 138 of basket 132 from the environment within lower testing chamber 50.

As transfer mechanism 110 is lowered, FIG. 8, from the raised position, FIG. 7, to the lowered position, FIG. 9, seal 130 disengages from the lower panel 44 of insulation wall 24. Further, basket 132 is slidably guided along supports 118 towards lower sealing panel 116 upon the engagement of lower surface 126 of lower sealing panel 116 with inner panel 32 of lower wall 20. In the lowered position, FIG. 9, upper sealing panel 114 overlaps opening 26 in insulation wall 24 such that seal 124 engages upper panel 42 of insulation wall 24 so as to isolate the environment in lower testing chamber 50 from the environment in upper testing chamber 48. In addition, lower basket panel 136 abuts upper surface 128 of lower sealing panel 116 and lower sealing panel 116 abuts inner panel 32 of lower wall 20 of body portion 12 of environmental test apparatus 10. An air gap 150 is defined between upper basket panel 134 and lower surface 122 of upper sealing panel 114 in order to provide the necessary insulation space to further isolate the product within product receipt cavity 138 of basket 132 from the environment within upper testing chamber 48.

As described, the height $H_2$ of product receipt cavity 138 of basket 132 exceeds the height H of the product receipt cavity 98 in prior art basket 92 by the height $HW_1$ of vertical wall 45. Hence, the volume of product receipt cavity 138 in basket 132 is greater than in prior baskets. As a result, transfer mechanism 110 allows for additional product to be simultaneously tested within environmental test apparatus as compared to prior such transfer mechanisms.

Various modes of carrying out the invention are contemplated as being within the scope of the following claims particularly pointing out and distinctly claiming the subject matter which is regarded as the invention.

We claim:

1. An apparatus for conducting environmental tests on a device, comprising:
   a cabinet defining first and second testing chambers therein;
   an insulation wall extending between the testing chambers and having an opening therein so as to allow passage between the first and second testing chambers;
   a sealing structure positioned within the cabinet and including first and second sealing members interconnected by a support element, the sealing structure movable between a first position wherein the first sealing member engages a first side of the insulation wall and overlaps the opening therein and a second position wherein the second sealing member engages a second side of the insulation wall and overlaps the opening therein; and
   a basket for carrying the device to be tested, the basket movable along the support element of the sealing structure between a first position in which the first sealing member engages the first side of the insulation wall to isolate the first testing chamber and the basket therein from the second testing chamber and a second position in which the second sealing member engages the second side of the insulation wall to isolate the first testing chamber from the second testing chamber and the basket therein.

2. The apparatus of claim 1 further comprising an actuator extending through one of the sealing members and being interconnected to the basket, the actuator controlling movement of the basket between the first and second positions.

3. The apparatus of claim 1 further comprising a control structure operatively connected to the cabinet for independently controlling the environmental conditions within each testing chamber.

4. The apparatus of claim 1 wherein the first sealing member includes a generally flat plate having a seal affixed thereto, the seal of the first sealing member engaging the first side of the insulation wall with the sealing structure in the first position.

5. The apparatus of claim 4 wherein the second sealing member includes a generally flat plate having a seal affixed thereto, the seal of the second sealing member engaging the second side of the insulation wall with the sealing structure in the second position.

6. An apparatus for conducting environmental tests on a device, comprising:
   a cabinet defining first and second testing chambers therein;

an insulation wall extending between the testing chambers and having an opening therein so as to allow passage between the first and second testing chambers;

a sealing structure positioned within the cabinet and including first and second sealing members interconnected by a support element, the support element including a shaft extending between the first and second sealing members, the sealing structure movable between a first position wherein the first sealing member engages a first side of the insulation wall and overlaps the opening therein and a second position wherein the second sealing member engages a second side of the insulation wall and overlaps the opening therein; and a basket for carrying the device to be tested, the basket movable along the support element of the sealing structure between a first position in which the first sealing member engages the first side of the insulation wall to isolate the first testing chamber from the second testing chamber and a second position in which the second sealing member engages the second side of the insulation wall to isolate the first testing chamber from the second testing chamber.

7. The apparatus of claim 6 wherein the basket includes a guide therethrough, the shaft of the support structure extending through the guide in order to guide the basket between the first and second positions.

8. An apparatus for conducting environmental tests on a device, comprising:

a cabinet defining first and second testing chambers therein;

an insulation wall disposed in the cabinet between the testing chambers, the insulation wall including first and second spaced panels interconnected by a third panel of predetermined length and being perpendicular to the first and second panels so as to define an opening in the insulation wall which allows passage between the first and second testing chambers;

a frame structure positioned within the cabinet and including first and second sealing panels interconnected by at least one support having a predetermined length, the frame structure movable between a first position wherein the first sealing panel engages the first panel of the insulation wall and overlaps the opening therein and a second position wherein the second sealing panel engages the second panel of the insulation wall and overlaps the opening therein; and a basket supported by the frame structure for carrying the device to be tested, the basket having a length, depth and height which is generally equal to the difference between the length of the at least one support of the frame structure and the length of the third panel of the insulation wall.

9. The apparatus of claim 8 wherein the basket is slidable along the at least one support of the frame structure between a first position adjacent the first sealing panel and a second position adjacent the second sealing panel.

10. The apparatus of claim 9 wherein the basket includes a guide therethrough, the shaft of the support structure extending through the guide in order to guide the basket between the first and second positions.

11. The apparatus of claim 9 further comprising an actuator extending through one of the sealing members and being interconnected to the basket, the actuator controlling movement of the basket between the first and second positions.

12. The apparatus of claim 8 further comprising a control structure operatively connected to the cabinet for independently controlling the environmental conditions within each testing chamber.

13. The apparatus of claim 8 wherein the first sealing panel includes a seal affixed thereto, the seal of the first sealing panel engaging the first panel of the insulation wall with the frame structure in the first position.

14. The apparatus of claim 13 wherein the second sealing panel includes a seal affixed thereto, the seal of the second sealing panel engaging the second panel of the insulation wall with the frame structure in the second position.

15. In an environmental testing apparatus for testing a device, the environmental testing apparatus having a cabinet defining first and second testing chambers and an insulation wall therebetween, the insulation wall having an opening therein so as to allow passage between the first and second testing chambers, the improvement comprising:

a frame structure positioned within the cabinet, the frame structure including first and second sealing panels interconnected by at least one support; and a basket for carrying the device to be tested, the basket slidable along the at least one support of the frame structure between a first position adjacent the first sealing panel and a second position adjacent the second sealing panel.

16. The improvement of claim 15 wherein the frame structure movable between a first position wherein the first sealing panel engages a first side of the insulation wall and overlaps the opening therein and a second position wherein the second sealing panel engages a second side of the insulation wall and overlaps the opening therein.

17. The improvement of claim 16 wherein the first sealing panel includes a seal affixed thereto, the seal of the first sealing panel engaging the first panel of the insulation wall with the frame structure in the first position.

18. The improvement of claim 17 wherein the second sealing panel includes a seal affixed thereto, the seal of the second sealing panel engaging the second panel of the insulation wall with the frame structure in the second position.

19. The improvement of claim 15 wherein the basket includes a guide therethrough, the support of the frame structure extending through the guide and guiding the basket between the first and second positions.

20. The improvement of claim 15 further comprising an actuator extending through one of the sealing panels and being interconnected to the basket, the actuator controlling movement of the basket between the first and second positions.

* * * * *